(12) United States Patent
Zech et al.

(10) Patent No.: US 6,677,393 B1
(45) Date of Patent: Jan. 13, 2004

(54) SILICON-BASED IMPRESSION COMPOUNDS WITH IMPROVED NON-SAG PROPERTIES

(75) Inventors: Joachim Zech, Seefeld (DE); Erich Wanek, Kaufering (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/937,911

(22) PCT Filed: Mar. 31, 2000

(86) PCT No.: PCT/EP00/02854

§ 371 (c)(1),
(2), (4) Date: Oct. 1, 2001

(87) PCT Pub. No.: WO00/59453

PCT Pub. Date: Oct. 12, 2000

(30) Foreign Application Priority Data

Apr. 1, 1999 (DE) .......................... 199 15 064

(51) Int. Cl.[7] ................................. C08K 5/06
(52) U.S. Cl. ................. 524/366; 524/588; 525/479; 528/15; 528/31; 528/32
(58) Field of Search ................ 524/588, 366; 528/15, 31, 32; 525/479

(56) References Cited

U.S. PATENT DOCUMENTS

| | | | |
|---|---|---|---|
| 5,108,782 A | * 4/1992 | Reed | 427/515 |
| 5,750,589 A | * 5/1998 | Zech et al. | 523/109 |
| 5,830,951 A | 11/1998 | Fiedler | |
| 6,121,368 A | * 9/2000 | Heying et al. | 524/493 |
| 6,448,329 B1 | * 9/2002 | Hirschi et al. | 524/588 |
| 2003/0143408 A1 | * 7/2003 | Benayoun et al. | 428/447 |

FOREIGN PATENT DOCUMENTS

| | | | | |
|---|---|---|---|---|
| DE | 3721784 C2 | 1/1988 | | |
| DE | 3721784 A1 | 1/1988 | | |
| DE | 19517962 A1 | 11/1996 | | |
| DE | 19728271 A1 | 1/1998 | | |
| EP | 231420 A1 | * 8/1987 | ......... A61K/6/10 |
| EP | 00268347 A1 | 5/1988 | | |
| EP | 0287092 | 10/1988 | | |
| EP | 0421371 B1 | 4/1991 | | |
| WO | 87 03001 A | 5/1987 | | |
| WO | 96 26246 | 8/1996 | | |
| WO | 98 41579 A1 | 9/1998 | | |

OTHER PUBLICATIONS

W. Gerhartz et al.: "Ullman's Encyclopedia of Industrial Chemistry, vol. A 8" 1987, VCH Verlag, Weinheim, DE XP002143931 Seite 289, linke Spalte.

* cited by examiner

Primary Examiner—Robert Dawson
Assistant Examiner—Marc S Zimmer
(74) Attorney, Agent, or Firm—Birch, Stewart, Kolasch & Birch, LLP

(57) ABSTRACT

The invention relates to silicone-based addition-crosslinking impression material, containing (a) organopolysiloxanes with at least two unsaturated groups in the molecule,
(b) organohydrogen polysiloxanes with at least three Si—H groups in the molecule,
(c) optionally, organopolysiloxanes without reactive groups,
(d) platinum catalyst,
(e) optionally, hydrophilizing agent,
(f) filler,
(g) optionally, further customary additives, auxiliaries and dyes, characterized in that it contains, as component (h), polyalkylene oxide and/or its derivatives with an average molar mass of $M_w > 1000$ at the rate of 0.001 to 1.0 wt.-% relative to the total mass of the cured material.

11 Claims, 1 Drawing Sheet

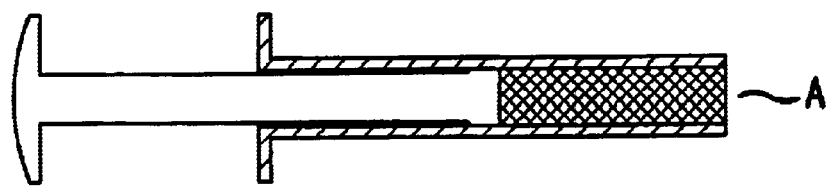
DIAGRAM 1
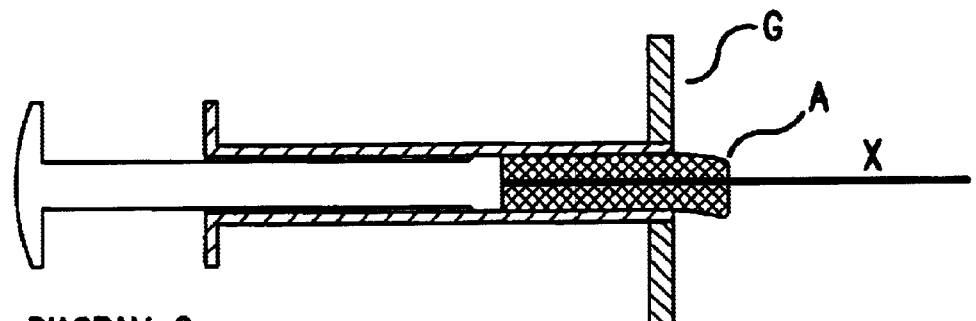
DIAGRAM 2
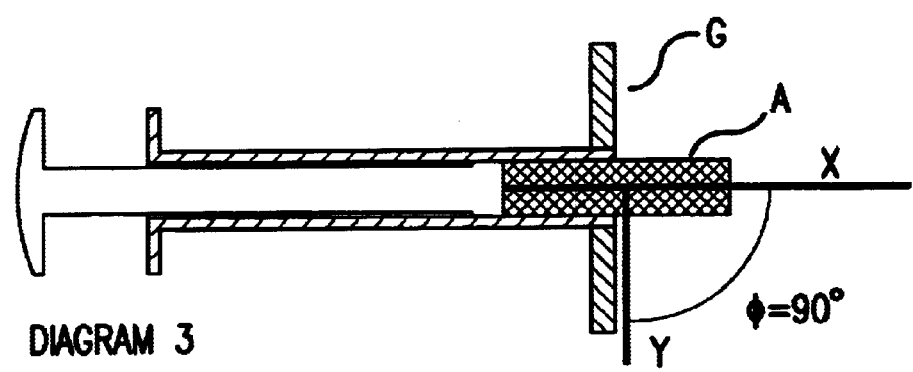
DIAGRAM 3
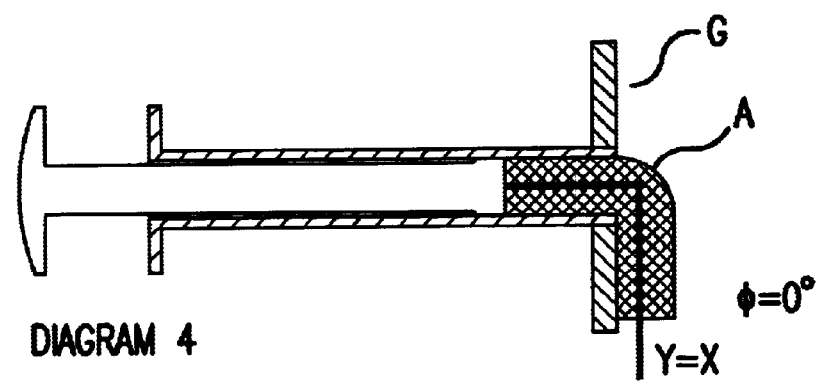
DIAGRAM 4

SILICON-BASED IMPRESSION COMPOUNDS WITH IMPROVED NON-SAG PROPERTIES

This application is the national phase under 35 U.S.C. §371 of PCT International Application No. PCT/EP00/02854 which has an International filing date of Mar. 31, 2000, which designated the United States of America and was not published in English.

The invention relates to silicone-based impression compositions with improved dimensional stability. The invention relates in particular to dental A-silicone impression compositions, the dimensional stability of which was increased by adding small amounts of polyalkylene oxides and/or their derivatives with an average molar mass of $M_w > 3000$.

In dentistry, dentures are made using models. To this end, a three-dimensional negative of the jaw situation is initially prepared by means of an impression composition, with, for example, the plastic, not yet set, impression composition being inserted into the patient's mouth on an impression cup and setting there. It is also possible to initially spray the points of the jaw which are to be modelled particularly accurately, with impression composition from a so-called elastomer syringe, and only then to introduce a cup filled with impression composition into the patient's mouth for the final cast. The impression composition ultimately sets to a hard or elastic composition which, following removal, represents the negative mould mentioned at the outset.

The most varied material classes are used as elastic impression materials, for example polyethers and silicones which are crosslinked by a chemical reaction to form the elastomer. Condensation and addition-crosslinking systems can be obtained with the silicones. The condensation-crosslinking silicones (C-silicones) crosslink as a rule through titanium- or tin-catalyzed reaction of the hydroxy-terminated polysiloxane with silicon alkoxy compounds accompanied by splitting off of an alcohol (condensation). In the case of the addition-crosslinking silicones (A-silicones), the crosslinking takes place as a rule through platinum-catalyzed reaction of unsaturated hydrocarbon terminal groups of the polysiloxane with Si—H groups of a hydrogen polysiloxane (hydrosilylation, addition). A-silicone impression compositions are known for example from EP-A-0 162 211, DE-A-40 31 759 and EP-A-0 166 107 as well as from the specialist literature, for example R. G. Graig, Restaurative Dental Materials, The C. V. Moosbe-Comp., St. Louis, 1980, p. 195ff.

The silicone compositions are usually supplied as a two-component system—in the form of separately packed base and catalyst pastes—the components being automatically or manually dosed in a specific mixing ratio before use, mixed and then introduced into the patient's mouth. They then cure there within a preset period of a few minutes.

In general, the base pastes are mostly composed of vinyl-terminated silicone oil, filler and crosslinkers and the catalyst pastes of vinyl-terminated silicone oil, filler and catalyst.

A disadvantage of many known silicone compositions is that they have a relatively low dimensional stability in the non-cured state. Attempts are made to deal with this disadvantage through various possibilities:

High degree of fill of the pastes with coarse inorganic fillers

Addition of pyrogenic silicic acids or of diatomaceous earth (WO-96/32088)

Addition of waxes (DE-A-195 17 962)

A disadvantage of these solutions is however that, on the one hand, poor flowability or insufficient precision of drawing, caused by the filler itself, is ascertained and, on the other hand, the additions tend to bleed, as they are added in not inconsiderable quantities, in the case of DE-A-195 17 962 of up to 40 wt.-%. A decrease in the Shore hardness and a deterioration in cuttability as well as storage stability have also been observed.

Furthermore, a practical disadvantage is that pastes with a high filler content or viscous additives such as waxes, can be ejected from their containers only with difficulty. Under certain conditions, it is no longer possible for the dentist or his assistant to dispense the pastes with one hand. Electrically-powered mixing apparatuses can cause damage if the ejection forces increase too greatly.

As high a dimensional stability as possible is necessary for example with bite registrations. A high dimensional stability is also desirable in the case of impression compositions for all other indications, in order that the non-set composition does not flow out of the impression cup into the patient's pharynx upon introduction into the patient's mouth and thus cause retching or in order that, upon spraying of individual jaw parts, the compositions do not drip due to gravity in the case of the upper jaw or flow away in the case of the lower jaw, and expose the prepared point in the jaw where particular precision is required. It is therefore necessary to find possibilities for increasing the dimensional stability of impression compositions without the previously described disadvantages of high ejection forces and bleeding being observed.

Surprisingly, it was found that additions of 0.001 to 1.0 wt.-% of polyalkylene oxides and/or their derivatives with an average molar mass of $M_w > 3000$ to A-silicone impression compositions permanently increase the dimensional stability of these compositions without adversely affecting the ejectability and Shore hardness.

The impression material according to the invention contains the following components:

(a) organopolysiloxanes with at least two unsaturated groups in the molecule, (b) organohydrogen polysiloxanes with at least three Si—H groups in the molecule, (c) optionally, organopolysiloxanes without reactive groups, (d) platinum catalyst, (e) optionally, hydrophilizing agent, (f) filler, (g) optionally, further customary additives, auxiliaries and dyes, (h) polyalkylene oxides and/or their derivatives with an average molar mass of $M_w > 3000$ at the rate of 0.001 to 1.0 wt.-% relative to the total mass of the cured material.

In the drawings there are shown in:

Diagram 1: an elastomer syringe, sawn off at the tip, which is filled with mixed impression composition (A), Diagram 2: Impression composition (A) projecting over the edge of the glass plate (G), in which the syringe is mounted, in direction (X) parallel to the syringe, Diagram 3: Representation of the angle ($\phi$)=90° between a parallel (Y) of the glass plate (G) and an idealized straight line (X) through the strand of the dispensed impression composition (A)

Diagram 4: Representation of the angle ($\phi$)=0° between a parallel (Y) of the glass plate (G) and an idealized straight line (X) through the strand of the dispensed impression composition (A).

The use in principle of additions to silicic-acid-containing silicone oil systems to influence their dimensional stability is generally known. In the brochure "Additives for CAB-O-SIL®", CABOT GmbH, Hanau, a listing of the most varied additive classes for the various objectives is given. The use according to the invention of polymeric polyalkylene oxides and/or their derivatives with an average molar mass $M_w > 3000$ to solve the problem posed here is not however described there, nor is it suggested by this brochure.

Preferred as component (a) are diorganopolysiloxanes with terminal triorganosiloxy groups of which at least one of the three organic groups is a vinyl group. Preferred diorganosiloxanes of this structure are reproduced by the following formula (1):

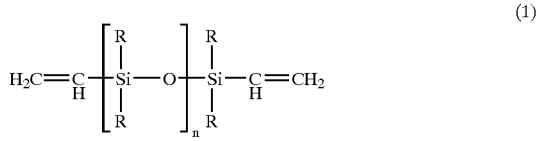

in which R represents an unsubstituted or substituted monovalent hydrocarbon group which is preferably free from aliphatic multiple bonds and n is an integer. At least 50% of the R radicals are preferably methyl groups. Examples of other R groups are ethyl, vinyl and 3,3,3-trifluoropropyl groups. The value of n is to be such that the polymer has a viscosity between 200 to 200,000 mPa·s, preferably 1000 to 10,000 mPa·s, at 25° C. Such molecules are described in U.S. Pat. No. 4,035,453, the disclosure of which is to be covered here in this respect.

The preparation of component (a) takes place according to customary processes which are shown e.g. in W. Noll "Chemie und Technologie der Silikone", Verlag Chemie Weinheim, $2^{nd}$ edition 1964, pages 162–206 or J. Burghardt, Chemie und Technologie der Polysiloxane in "Silikone, Chemie und Technologie", Vulkan Verlag, Essen, 1989, pages 23–37.

Particularly preferred are linear polydimethylsiloxanes of the above structure with the given viscosity ranges in which the terminal groups are composed of dimethylvinylsiloxy units and the further R substituents in the chain are composed of methyl groups.

Component (b) is preferably an organopolysiloxane with at least three Si-bound hydrogen atoms per molecule. This organopolysiloxane preferably contains from 0.01 to 1.7 wt.-% silicon-bound hydrogen. The silicone valencies which are not saturated with hydrogen or oxygen atoms are saturated with monovalent hydrocarbon radicals which are free from aliphatic multiple bonds. The hydrocarbon radicals can be substituted or unsubstituted. At least 50%, preferably 100%, of the hydrocarbon radicals which are bound to silicon atoms are composed of methyl radicals. Such components are also described in the above-named literature references with regard to structure and preparation.

The quantity ratios of components (a) and (b) are preferably chosen such that 0.75 to 5 mol of Si—H units from component (b) are present per mol of unsaturated double bond of component (a). The sum of components (a) and component (b) lies in the range from 10 to 40 wt.-% relative to the total weight of all components. Preferably, they lie in the range from 15 to 30 wt.-%.

Suitable components (c) are polymeric organosiloxanes without reactive substituents such as described e.g. in W. Noll "Chemie und Technologie der Silikone", Verlag Chemie Weinheim, 1968, page 212 ff. They are preferably linear, branched or cyclic organopolysiloxanes in which all silicon atoms are surrounded by oxygen atoms or monovalent hydrocarbon radicals, where the hydrocarbon radicals can be substituted or unsubstituted. The hydrocarbon radicals can be methyl, ethyl, $C_{2-10}$ aliphatics, trifluoropropyl groups, as well as aromatic $C_6$–$C_{12}$ substituents. Component (c) contributes to the dilution and expansion of the network and acts as plasticizer for the cured material. As a relatively cheap component, it also contributes to the reduction of the preparation costs of the impression compositions according to the invention.

Particularly preferred as component (c) are polydimethyl siloxanes which have trimethylsiloxy terminal groups. The viscosity of component (c) preferably lies in the range from 10 to 20,000 mPa·s, particularly preferably 10 to 1,000 mPa·s. The quantity of component (c) is 0 to 40 wt.-%, preferably 5 to 40 wt.-%, particularly preferably 15 to 30 wt.-%.

Component (d) is preferably a platinum complex which was prepared from hexachloroplatinic acid by reduction with tetramethyldivinyldisiloxane. These compounds are known per se. Also suitable are other platinum compounds which accelerate the addition crosslinking. Well suited are e.g. platinum-siloxane complexes such as described for example in U.S. Pat. Nos. 3,715,334, 3,775,352 and 3,814,730. The platinum catalyst is used in quantities of 0.00005 to 0.05 wt.-%, preferably 0.0002 to 0.04 wt.-% calculated in each case as elementary platinum and relative to the total weight of the composition present with the components (a) to (h). To control the reactivity, it may be necessary that an inhibitor must be added which prevents the premature crosslinking to the elastomer. Such inhibitors are known and described e.g. in U.S. Pat. No. 3,933,880.

Examples of these are acetylenically unsaturated alcohols, such as 3-methyl-1-butine-3-ol, 1-etninylcyclohexane-1-ol, 3,5-dimethyl-1-hexine-3-ol and 3-methyl-1-pentine-3-ol. Examples of vinylsiloxane-based inhibitors are 1,1,3,3-tetramethyl-1,3-divinylsiloxane and vinyl-group-containing poly-, oligo- and disiloxanes.

The compositions according to the invention cured after mixing are not hydrophilic and, without the addition of hydrophilizing agents, have a contact and/or wetting angle which is preferably greater than 70°, particularly preferably greater than 80°. Optionally, therefore, component (e) is added to the compositions as an agent which bestows a hydrophilic nature or a hydrophilizing agent which reduces the wetting angle of a drop of water or aqueous composition (e.g. plaster suspension, etc.) vis-à-vis the silicone composition and thus produces a better wettability of the total composition in the moist mouth environment and thus a better flow behaviour of the pastes. The hydrophilizing agents are preferably not provided with reactive groups, so that no incorporation into the polysiloxane network takes place. Suitable hydrophilizing agents are preferably non-incorporable wetting agents from the group of hydrophilic silicone oils which are described in WO-87/03001 and in EP-B-0 231 420, reference to the disclosure of which is to be made here in this respect. Also preferred are the ethoxylated fatty alcohols which are described in EP-B-0 480 238. Further preferred hydrophilizing agents are the polyether carbosilanes known from WO-96/08230. Also preferred are the non-ionic perfluoroalkylated surfactants described in WO-87/03001. Also preferred are the non-ionic surfactants which are described in EP-B-0 268 347, i.e. the nonylphenol ethoxylates, polyethylene glycol mono- and diesters, sorbitan esters, as well as polyethleneglycol mono- and diethers listed therein. The quantities of hydrophilizing agents used are 0 to 10 wt.-%, relative to the total weight of all components, preferably 0 to 2 wt.-% and particularly preferably 0 to 1 wt.-%.

The wetting angle is measured according to the lying drop method according to DE-A 4433139. Measurement is with a G1/G40 contact angle measurement system (Kruss). This measurement apparatus makes possible the precise modelling of drop profiles on surfaces of solids. The measurement system furthermore includes a video tube with beam splitter, so that the simultaneous observation of a drop through the goniometer eyepiece (drop size) and the video camera (digital image evaluation) is made possible. The measurement is carried out on the lying drop at 23° C. and 50% relative air humidity, 30 minutes after the mixing of the compositions has begun, a drop always of the same size of calcium sulphate dihydrate solution saturated at 23° C. is deposited on the elastomer that has cured to a smooth surface between glass plates and the measurement is begun immediately. The 10-second value is used for evaluation.

Component (h) is a polyalkylene oxide and/or derivative with an average molar mass $M_w$>3000. Molecules according to the invention are those containing either chemically inert or reactive terminal groups.

To measure the molar mass of the compounds according to component (h), methods known to a person skilled in the art can be used in relation to the presence of reactive terminal groups and the molar mass, for example terminal-group determination, measurement of the osmotic pressure, isothermal distillation (method of the isopiestic solutions), counting by means of electron microscopy, diffusion measurement, sedimentation, ultra-centrifuging, precipitation and turbidity titration, measurement of viscosity, light scattering dialysis rate. Suitable methods in the measurement of the molar mass of reactive terminal groups, for example OH group-containing polyalkylene oxides, include the titration of the terminal groups according to DAB 10 as measurement of the hydroxyl count. This method has been used within the framework of the present invention for polyalkylene oxides according to component (h). For polyalkylene oxide derivatives according to component (h), the same method can be used after prior transformation of the terminal groups into titratable groups.

Preferred representatives of component (h) are polyalkylene oxide derivatives according to EP-B-0 421 371, the disclosure of which is to be expressly included here with reference to the polyalkylene oxide derivatives (R≠H), as well as polyalkylene oxides to be derived therefrom (R=H). Both substances follow the given general formula (2):

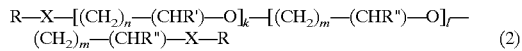

in which:
- n=1 to 6, preferably 1 to 4, in particular 1, n being able to vary within the chain,
- m=1 to 6, preferably 1 to 4, in particular 3, m being able to vary within the chain,
- k, l=2 to 500, preferably 4 to 250, in particular 10 to 200,
- R',R''=H, methyl, ethyl, preferably R'=R''=H,
- X=S, O, NH, preferably O,
- R=H or $C_{1-18}$, preferably $C_{1-12}$, in particular $C_{1-8}$ alkyl, particularly preferably $C_{1-3}$ alkyl, or carbonyl $C_{1-17}$, preferably carbonyl $C_{1-11}$, in particular carbonyl $C_{1-5}$ alkyl, particularly preferably carbonyl $C_{1-3}$ alkyl, or a radical of the general formula (3):

where R'''=$C_{1-18}$, preferably $C_{1-12}$, in particular $C_{1-6}$ alkyl, particularly preferably $C_{1-3}$ alkyl and/or $C_{6-18}$ aryl, preferably $C_{6-12}$ aryl and X has the meaning given above and p=0 or 1, p=0 being preferred, and where R is preferably not H,
the bracketed expressions indexed by the symbols k and l being able to be arranged regularly or irregularly alternating or in block form.

A particularly preferred representative of this is the diacetate of the following formula (4) which belongs to the chemically inert variants:

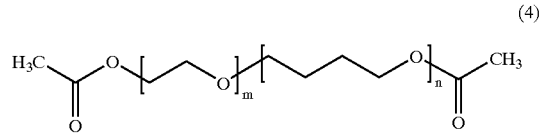

or the derivative of formula (5)

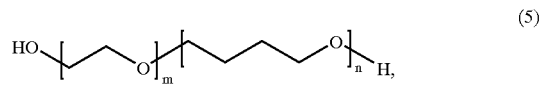

the ratio of m:n lying in the range from 1:3 to 1:4. The average molar mass $M_w$ is preferably ≈6000.

Further preferred are block copolymers of propylene oxide and ethylene oxide such as, say, derivatives of propylene glycol and of ethylenediamine which are marketed by Wyandotte under the names Pluronics and Tetronics. Also possible are ethoxylated polypropylene oxides of various chain lengths (synperonic types), SB 169 P (Goldschmidt polyethers) as well as Tegopren-7006.

The polyalkylene oxides according to the invention preferably have no surfactant character. In addition, they are preferably derivatized so that they cannot enter into reactions with components of the matrix, in particular via OH or NH groups.

Within the compositions according the invention, mixtures of various representatives of component (h) can naturally also be used. The total content of component (h) is 0.001 to 1.0 wt.-%, preferably 0.01 to 0.5 wt.-% and particularly preferably 0.02 to 0.3 wt.-%, in each case relative to the total weight of the composition.

The fillers which can be used according to component (f) include non-reinforcing fillers with a BET surface of up to 50 m²/g such as quartz, cristobalite, calcium silicate, zirconium silicate, montmorillonites such as bentonites, zeolites, including the molecular sieves, such as sodium aluminium silicate, metal oxide powders, such as aluminium or zinc oxides or their mixed oxides, barium sulphate, calcium carbonate, plaster, glass and plastic powders. Possible fillers also include reinforcing fillers with a BET surface of more than 50 m²/g such as e.g. pyrogenic or precipitated silicic acid and silicon aluminium mixed oxides with a large BET surface. The named fillers can be hydrophobized, for example by treatment with organosilanes or siloxanes or by the etherification of hydroxyl groups to alkoxy groups. One type of filler, also a mixture of at least two fillers can be used. The grain distribution is preferably chosen such that no fillers with grain sizes >50 μm are contained. The overall content of the fillers (f) lies in the range from 10 to 79.99895 wt.-%, preferably 30 to 60 wt.-%, relative the total weight of the material.

Particularly preferred is a combination of reinforcing and non-reinforcing fillers. The reinforcing fillers lie in quantity ranges from 1 to 10 wt.-%, in particular 2 to 5 wt.-%. The difference to the named overall ranges, i.e. 9 to 69.99895 wt.-%, in particular 28 to 55 wt.-% is formed by the non-reinforcing fillers.

Preferred as reinforcing fillers are pyrogenically prepared highly-dispersed silicic acids which have preferably been hydrophobized by surface treatment. The surface treatment can take place for example with dimethyldichlorosilane, hexamethyldisilazane, tetramethylcyclotetrasiloxane or polymethylsiloxanes. The surfaces of suitable pyrogenic silicic acids are preferably >50 m$^2$/g, in particular 80 to 150 m$^2$/g. The presence of the surface-treated pyrogenic silicic acids contributes to the setting of the consistency and to the improvement of the dimensional stability of the pastes. With quantities of <1 wt.-%, as a rule, no noticeable influence on dimensional stability is to be found. Quantities of >10 wt.-% lead as a rule to too strong a thickening of the pastes, so that sufficient flowability can no longer be obtained.

Suitable products are described for example in the brochures of Degussa (Aerosil products, Pigments series, no. II, 5$^{th}$ edition, 1991, on page 79) and Cabot Corp. (Cabosil products, "CAB-O-SIL Fumed silica in Adhesives and Sealants, Cabot, 1990).

Particularly preferred non-reinforcing fillers are quartz, cristobalites and sodium aluminium silicates which can be surface-treated. The surface treatment can in principle take place using the same methods as have been described in the case of the reinforcing fillers.

Furthermore, the impression compositions according to the invention can optionally contain as component (g) additives such as plasticizers, pigments, antioxidants, mould-release agents, among others. Likewise, finely-distributed palladium or platinum can also be contained as hydrogen-absorber. The metals can also be deposited on support materials. The compositions according to the invention contain such additives in quantities of preferably 0 to 2 wt.-%, particularly preferred of 0.1 to 1 wt.-%.

The compositions are prepared by mixing components (a) to (h) and cure in an addition reaction called hydrosilylation, in which the Si—H groups of component (b) are added to the unsaturated groups of component (a) under the influence of the platinum catalyst (d). For reasons of storage stability, it is preferred to formulate the compositions in a two-component administration form in which the total component (b) is housed in a so-called base paste. The total component (d) is housed, physically separated from this, in a so-called catalyst paste. Component (a) can be housed in either the catalyst or base paste, a part each of component (a) preferably being housed in the base, and part of component (a) in the catalyst, paste. Components (c), (e), (f), (g) and (h) can be housed in their total quantity in the catalyst or in the base paste, it being preferred that a part of each of the respective component is housed in the catalyst and a part in the base paste. It is particularly preferred that components (e) and (h) are contained only in the base paste.

The volume ratios of catalyst and base pastes can be 10:1 to 1:10. Particularly preferred volume ratios of base: catalyst paste are 1:1 and 5:1 (5 parts base paste: 1 part catalyst paste).

The invention is to be explained in more detail in the following by means of examples without being limited by them.

Preparation Example
Additive 600 g of a copolymer of tetrahydrofuran and ethylene oxide (in the ratio 2:1, molecular weight 6,000; within the framework of this application called "Diol 6000") are dissolved in 1.3 l cyclohexane. 19.4 g of acetic anhydride and 3.5 g toluenesulphonic acid are then added, and the whole heated for 4 hours under reflux. Working-up is by means of extraction twice with aqueous sodium hydroxide solution (2n), extraction once with aqueous sulphuric acid and extraction twice with distilled water. Drying is then carried out with sodium sulphate and the solvent is distilled off 500 g polyalkylene oxide bisacetate is obtained.

Comparison Example

Base and catalyst pastes are prepared analogously to the application example, but no representative of component (h) according to the invention is added. The dimensional stability measurement is carried out analogously to the following test.

Application Examples
Base Paste 24.9 g (l-ω-terminated polydimethylsiloxane with a viscosity of 200 mPa·s at 23° C., 3.2 poly(methyl) hydrogensiloxane with a viscosity of 35 mPa·s at 23° C, 2.0 g silicone oil with a viscosity of 50 mPa·s at 23° C. and 0.02 g pigment are mixed in a kneader together with 3.1 g silanized pyrogenic silicic acid and 66.6 g quartz.

Catalyst Paste 27.0 g (l-ω-terminated polydimethyl siloxane with a viscosity of 200 mPa·s at 23° C. and 2.0 g silicone oil with a viscosity of 50 mPa·s at 23° C. are mixed in a kneader together with 2.9 g silanized pyrogenic silicic acid, 68.0 quartz and 0.3 g platinum catalyst solution.

0.1 wt.-% additives are added according to Table (1) to the catalyst paste and the mixture is kneaded homogenously. Base and catalyst pastes are poured into a double-chambered cartridge and the dimensional stability of the individual impression compositions is determined according to the following test.

Comparison Example
State of the Art

Base and catalyst pastes are prepared analogously to the application example, but no representative of component (h) according to the invention is added, the quantity of Aerosil (silanized pyrogenic silicic acid) being increased by 2% instead. The dimensional stability measurement is carried out analogously to the following test.

Examination of Dimensional Stability

An elastomer syringe sawn off at the tip (diagram 1) is filled with mixed impression composition (A). The open end of the syringe is inserted into the bore of a glass plate (G) and, through pressure on the plunger, the impression composition (A) is pushed out of the syringe over the edge of the glass plate (G) in direction (X) (diagram 2). The dimensional stability of the impression composition counteracts gravity. The more dimensionally stable the material, the closer is the angle φ between a parallel (Y) to the glass plate (G) and an idealized straight line (X) through the dispensed strand of impression composition (A) to 90° (diagram 3). Specimens displaying little or no dimensional stability slide down along the glass wall (G) and form an angle of φ of 0° (diagram 4).

Examination of the Ejection Force

A double-chambered cartridge customary in the trade which is filled with the respective base and catalyst pastes is clamped in a universal testing machine (Zwick). No static mixer is fitted on it. Double-chambered cartridges are closed as with products customary in the trade on the base and catalyst sides in each case by a plastic stopper with a rubber ring as sealing lip. The pastes are ejected out of the cartridges in the testing machine by pressing a mould force onto the plastic stopper on the base and catalyst sides. The rate of feed was set at 50 mm/min and the pre-force at 10 N.

TABLE 1

Dimensional stability values and ejection forces

| Additive | Additive variant | Dimensional stability | Ejection force | Contact angle |
|---|---|---|---|---|
| None, comparison example | | 0° | 578N | >80° |
| Preparation example additive | Inert | 90° | 531N | >80° |
| Synperonic PE/L 121 (manufacturer ICI) | Not inert | 90° | 570N | >80° |
| Diol 6000 | Not inert | 90° | 543N | >80° |
| Polypropylene glycol $M_w \approx 4000$ | Not inert | 90° | 558N | >80° |
| None, comparison example state of the art | | 90° | 800N | >80° |

The addition of component (h) according to the invention leads to an increase in dimensional stability with an insignificant change in the ejection forces.

What is claimed is:

1. Silicone-based addition-crosslinking impression material, comprising
   a) organopolysiloxanes with at least two unsaturated groups in the molecule,
   b) organohydrogen polysiloxanes with at least three Si—H groups in the molecule,
   c) optionally, organopolysiloxanes without reactive groups,
   d) platinum catalyst,
   e) optionally, hydrophilizing agent,
   f) filler,
   g) optionally, further additives, auxiliaries and dyes,
wherein the impression material contains, as component (h) polyalkylene oxide and/or derivatives of polyalkylene oxide wherein said polyalkylene oxide and/or said derivatives of polyalkylene oxide have an average molar mass of $M_w > 3000$, do not contain Si atoms and are present at 0.001 to 1.0 weight % relative to the total mass of the cured material.

2. Impression material according to claim 1, containing
   10 to 40 wt.-% components (a)+(b)
   0 to 40 wt.-% component (c)
   0.00005 to 0.05 wt.-% component (d)
   0 to 10 wt.-% component (e)
   10 to 79.99895 wt.-% component (f)
   0 to 2 wt.-% component (g)
   0.001 to 1.0 wt.-% component (h)
each relative to the total weight of the composition.

3. Impression material according to one of claim 1 or 2, characterized in that component (h) represents a polyalkylene oxide or derivative of the general formula (2):

$$R-X-[(CH_2)_n-(CHR')-O]_k-[(CH_2)_m-(CHR'')-O]_l-(CH_2)_m-(CHR'')-X-R \quad (2)$$

n=1 to 6, n being able to vary within the chain,
m=1 to 6, m being able to vary within the chain,
k, l=2 to 500,
R', R''=H, methyl, ethyl,
X=S, O, NH,
R=H or $C_{1-18}$ alkyl, or carbonyl $C_{1-17}$ alkyl, or a radical of the general formula (3):

where $R'''=C_{1-18}$ alkyl and/or $C_{6-18}$ aryl and X has the meaning given above and p=0 or 1,
the bracketed expressions indexed by the symbols k and l being able to be arranged regularly or irregularly alternating or in block form.

4. Impression material according to claim 3, characterized in that the polyalkylene oxide derivative corresponds to the formula:

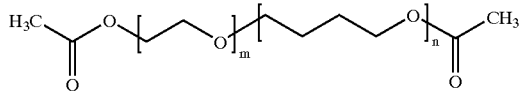

or the formula

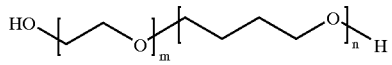

where the ratio of m:n=1:3 to 1:4.

5. Impression material according to one of claim 1 or 2, characterized in that the polyalkylene oxide or derivative represents a block copolymer of propylene oxide and ethylene oxide.

6. Impression material according to claim 1, characterized in that it is present in the form of a base paste and a catalyst paste physically separated from it, the total component (b) being present in the remaining components being distributed as desired in the two pastes.

7. A dental material made of the impression material according to claim 1.

8. The dental material of claim 7, wherein the dental material is a bite registration.

9. A silicone-based addition-crosslinking impression material, comprising
   a) organopolysiloxanes with at least two unsaturated groups in the molecule,
   b) organohydrogen polysiloxanes with at least three Si—H groups in the molecule, and
   c) polyalkylene oxide and/or derivatives of polyalkylene oxide wherein said polyalkylene oxide and/or said derivatives of polyalkylene oxide have an average molar mass of $M_w > 3000$, do not contain Si and are present at 0.001 to 1.0 weight % relative to the total mass of the cured material.

10. The silicone-based addition-crosslinking impression material of claim 9, which further comprises filler.

11. A method of increasing dimensional stability in silicone-based impression compositions comprising adding polyalkylene oxides and/or derivatives of polyalkylene oxide with an average molar mass $M_w > 3000$ to the silicone-based impression compositions, wherein curing is via a hydrosilylation pathway.

* * * * *

UNITED STATES PATENT AND TRADEMARK OFFICE
CERTIFICATE OF CORRECTION

PATENT NO. : 6,677,393 B1  Page 1 of 1
DATED : January 13, 2004
INVENTOR(S) : Zech, Joachim It is certified that error appears in the above-identified patent and that said Letters Patent is hereby corrected as shown below:

Column 4,
Line 35, delete "1-etninylcyclohexane" and insert -- 1-ethinylcyclohexane --.

Column 5,
Line 33, after "scattering" insert -- , --.
Line 35, after "OH" insert -- - --.
Lines 50-51, Formula 2, should read
-- R—X—[(CH$_2$)$_n$—(CHR')—O]$_k$—[(CH$_2$)$_m$—(CHR")—O]—(CH$_2$)$_m$—(CHR")—X—R --.

Column 6,
Lines 21-25, Formula 5, after " 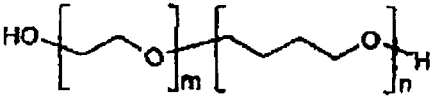 ", delete ",".

Column 8,
Lines 19 and 26, delete "(1-ω-terminated" and insert -- α-ω-terminated --.

Column 9,
Lines 59 and 60, Formula should read
-- R—X—[(CH$_2$)$_n$—(CHR')—O]$_k$—[(CH$_2$)$_m$—(CHR")—O]—(CH$_2$)$_m$—(CHR")—X—R --.

Signed and Sealed this

Twentieth Day of December, 2005

JON W. DUDAS
*Director of the United States Patent and Trademark Office*